United States Patent [19]

Christiansen

[11] Patent Number: 5,551,849
[45] Date of Patent: Sep. 3, 1996

[54] MEDICATION DELIVERY DEVICE AND METHOD OF CONSTRUCTION

[75] Inventor: Chris C. Christiansen, Oakdale, Minn.

[73] Assignee: Medtronic, Inc., Minneapolis, Minn.

[21] Appl. No.: 235,436

[22] Filed: Apr. 29, 1994

[51] Int. Cl.⁶ .................. F04B 45/033; A61M 5/152
[52] U.S. Cl. .................. 417/472; 604/141; 92/34
[58] Field of Search ................ 604/141, 132, 604/93, 891.1; 417/375, 472; 92/34, 43, 44

[56] References Cited

U.S. PATENT DOCUMENTS

| | | | |
|---|---|---|---|
| 1,097,124 | 5/1914 | Fulton | 92/34 |
| 2,083,943 | 6/1937 | Clifford | 92/34 |
| 3,422,680 | 11/1969 | Nolte | 92/34 |
| 3,731,681 | 5/1973 | Blackshear et al. | 128/214 R |
| 3,951,147 | 4/1976 | Tucker et al. | 128/260 |
| 4,193,397 | 3/1980 | Tucker et al. | 128/207.19 |
| 4,221,219 | 9/1980 | Tucker | 128/260 |
| 4,360,019 | 11/1982 | Portner et al. | 128/213 R |
| 4,581,018 | 4/1986 | Jassawalla et al. | 604/153 |
| 4,692,147 | 9/1987 | Duggan | 604/93 |
| 4,714,462 | 12/1987 | DiDomenico | 604/141 |
| 4,838,887 | 6/1989 | Idriss | 604/891.1 |
| 4,978,338 | 12/1990 | Melsky et al. | 604/93 |
| 5,061,242 | 10/1991 | Sampson | 604/118 |
| 5,088,983 | 2/1992 | Burke | 604/141 |
| 5,197,322 | 3/1993 | Indravudh | 604/141 |
| 5,201,643 | 4/1993 | Hirosawa et al. | 417/472 |
| 5,368,571 | 11/1994 | Horres, Jr. | 604/141 |
| 5,382,236 | 1/1995 | Otto et al. | 604/141 |
| 5,395,324 | 3/1995 | Hinrichs et al. | 604/132 |
| 5,443,450 | 8/1995 | Kratoska et al. | 604/141 |

Primary Examiner—Timothy S. Thorpe
Assistant Examiner—Peter G. Korytnyk
Attorney, Agent, or Firm—Curtis D. Kinghorn; Harold R. Patton

[57] ABSTRACT

A medication delivery device having a reduced weight due to the configuration of the end terminal of the pleated bellows reservoir. The end terminal includes an indented portion which is sized such that when the reservoir is in the compressed/empty position there is substantially no separation between the indented portion and the base portion of the reservoir. This construction allows the reservoir to be almost completely emptied of medication when the reservoir is collapsed but does so in a manner which does not add to the weight of the device.

9 Claims, 5 Drawing Sheets

MEDICATION DELIVERY DEVICE AND METHOD OF CONSTRUCTION

FIELD OF THE INVENTION

The present invention relates to medication delivery devices which are implanted within the body of a patient and methods of construction of the devices. More particularly, the invention relates to a medication delivery device having a reduced weight due to the configuration of the end terminal of the pleated bellows reservoir which includes an indented portion shaped to minimize dead space in the reservoir.

BACKGROUND OF THE INVENTION

The use of implantable fluid medication dispensers is well known. These devices typically include a medication reservoir within a generally cylindrically shaped housing. Some form of fluid flow control is also provided to control or regulate the flow of fluid medication from the reservoir to the outlet of the device for delivery of the medication to the desired location, usually through a catheter. The flow control may be provided by a pumping or metering device such as disclosed in U.S. Pat. No. 4,692,147 issued to Duggan. Other forms of flow control are disclosed in U.S. Pat. Nos. 3,951,147 and 4,360,019.

All implantable fluid medication dispensers must also include some means to replenish the fluid medication in the medication reservoir. The previously mentioned U.S. Pat. Nos. 4,692,147 to Duggan and 3,951,147 to Tucker et al. disclose typical reservoir refill assemblies. Both include an opening or port through which a resealable septum may be accessed. To refill the reservoir a hypodermic needle is inserted through the septum and into a chamber between the septum and a needle stop, which may be a plug or filter. The medication is injected under pressure into the chamber and flows into the Reservoir.

One disadvantage which exists with respect to currently used fluid medication dispensers is the weight of the devices. Weight is a critical factor with respect to both the physical and psychological comfort of the patient. In devices where the fluid medication reservoir is pleated such as in the typically used bellows configuration, in order to insure that the medication reservoir has minimal dead space when the convulsions of the pleats of the bellows are compressed, current devices utilize a bulkhead with a boss configured to mate with the interior of the bellows when compressed. This raised boss adds considerably to the overall weight of the fluid medication dispenser. Therefore, it would be desirable to provide a medication delivery device having a reduced weight.

SUMMARY OF THE INVENTION

The present invention is a medication delivery device having a reduced weight due to the configuration of the end terminal of the pleated medication reservoir. In one embodiment the invention is a medication delivery device which comprises a housing, a reservoir within the housing, a reservoir port in fluid communication with the reservoir, an outlet port and means connected between the reservoir and the outlet port for dispensing medication from the reservoir through the outlet port. The means for dispensing medication may be a flow regulator, a flow restrictor, a pump, a medication metering device or any other dispensing means. The reservoir has a peripheral pleated side portion or wall bounded on one end by an end terminal and on the other end by an opposing surface portion. The reservoir is movable from an expanded/full position to a compressed/empty position. The end terminal includes a surface portion which is indented in the direction of the opposing surface portion so that when the reservoir is in the compressed/empty position there is substantially no separation between the indented surface portion and the opposing surface portion. This allows the reservoir to be almost completely emptied of medication. The reservoir may include an aperture which is bounded by additional pleats and within which the reservoir refill port may be positioned.

When the reservoir is in the compressed position the pleated side portion is collapsed so that the distance between the end terminal and the opposing surface is equal to a distance T. The indented surface portion of the end terminal may be indented a distance approximately equal to distance T.

In another embodiment the invention is a medication delivery device comprising a housing, a bulkhead connected to the housing and having a base portion, a reservoir within the housing, a reservoir refill port in fluid communication with the reservoir, an outlet port and means connected between the reservoir and the outlet ports for dispensing medication from the reservoir through the outlet port. Again, the dispensing means may be a flow regulator, a flow restrictor, a pump, a medication metering device or any other dispensing means known to those skilled in the art. The reservoir includes a pleated side portion and an end terminal. The pleated side portion is connected to the base portion of the bulkhead so that the pleated side portion, the end terminal and the base portion together define an enclosed area to contain fluid medication. The reservoir is movable from an expanded position to a compressed position. The end terminal has a surface portion which is indented in the direction of the base portion so that when the reservoir is in the compressed position, there is substantially no separation between the indented surface portion and the base portion.

DESCRIPTION OF THE PREFERRED EMBODIMENTS

Figure 1:
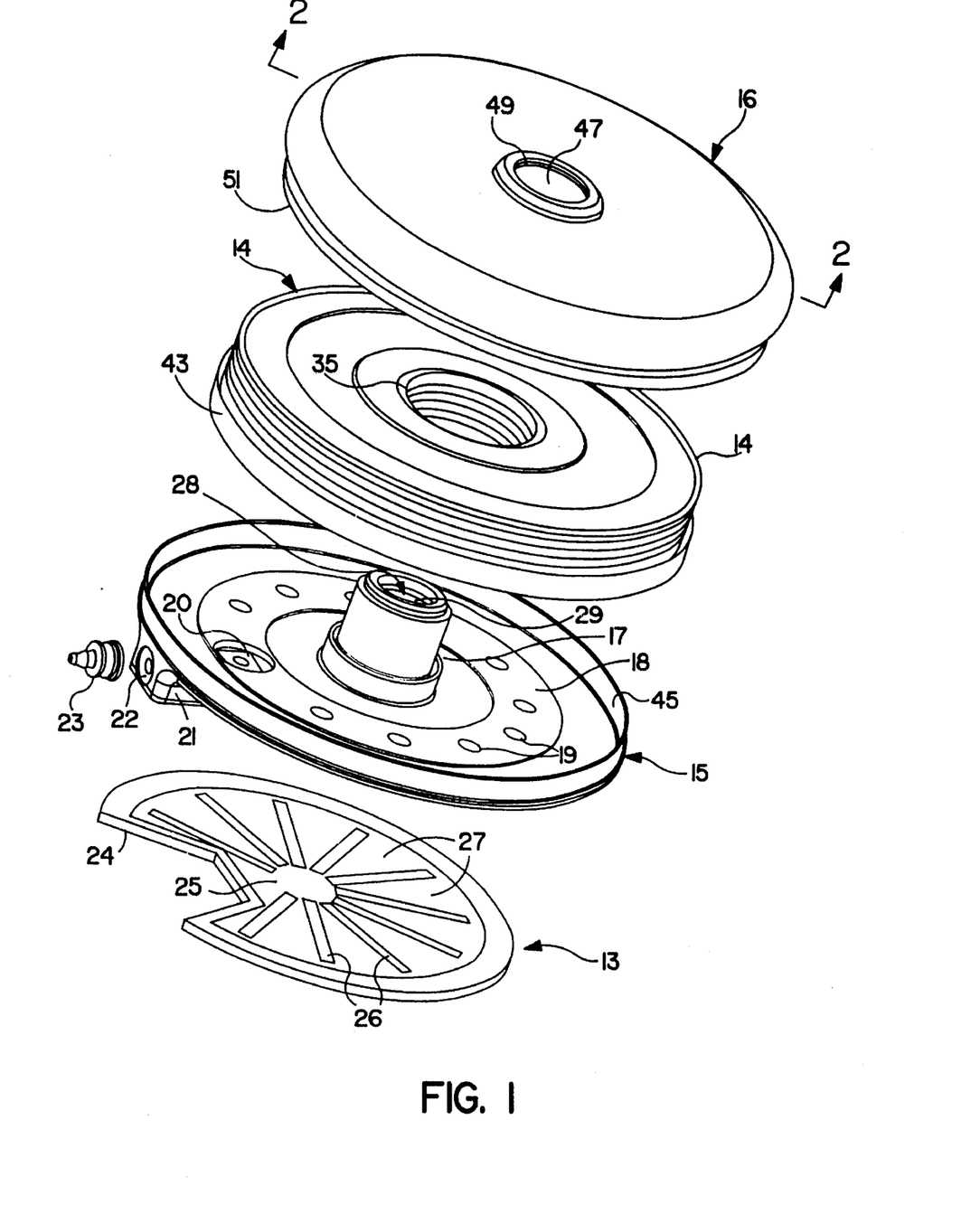
FIG. 1 is an exploded perspective view of one embodiment of the medication delivery device 10 of the present invention.
Figure 2:
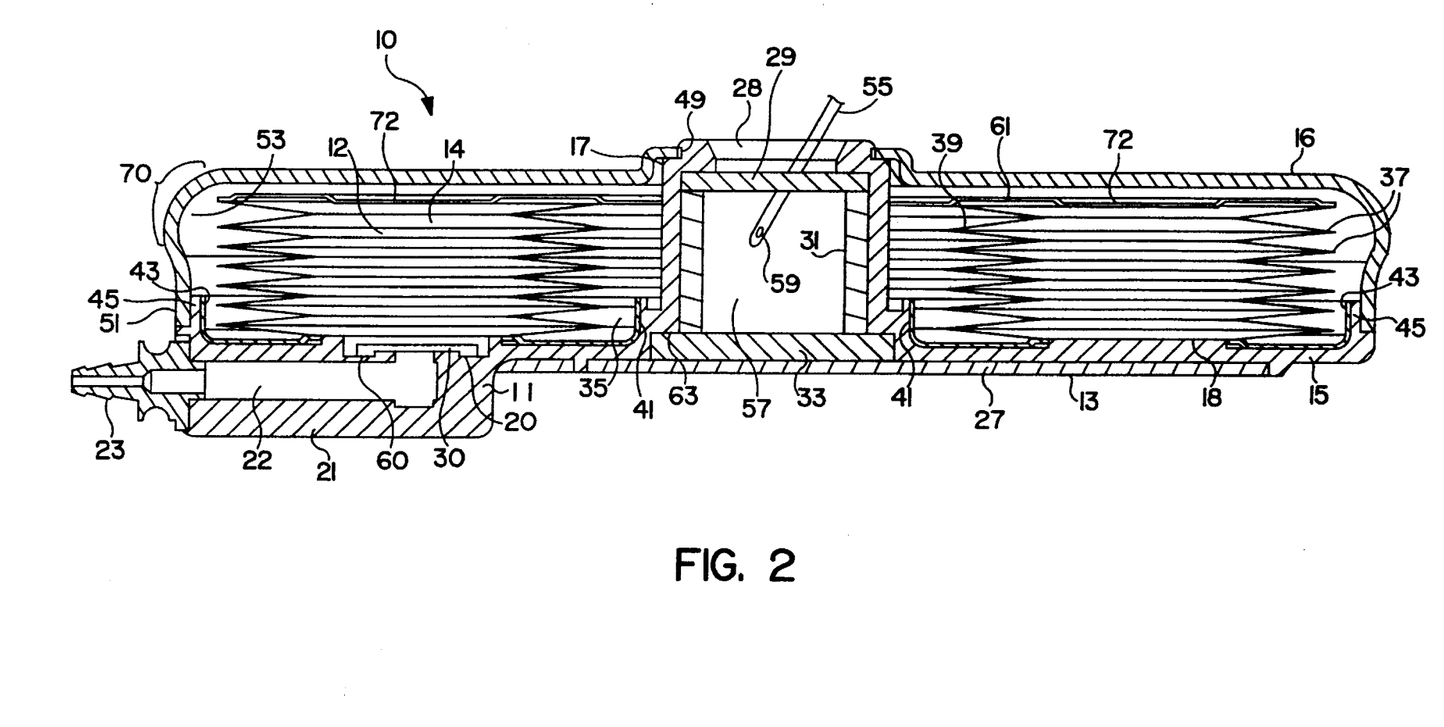
FIG. 2 is a cross-sectional view thereof, taken generally along line 2—2 of FIG. 1.

Referring now to FIGS. 1–2, a medication delivery device 10, for delivering a fluid medication 12, is illustrated. The term "medication" is used in its broad sense, and may be any fluid, whether or not the fluid is medicinal in nature. The term "fluid" is also used in its broad sense, and includes both liquids and gasses.

Turning again to FIGS. 1–2, the medication delivery device 10 may comprise five main components, namely, a manifold 13, a donut-shaped bellows reservoir 14, a bulkhead 15, a cover 16, and a flow regulator 30. Optionally, flow regulator 30 may be any type of flow restriction device such as capillary tubing. Additionally, it should be understood that although the embodiment of the invention disclosed in FIGS. 1 and 2 has a dispensing means consisting of a flow regulator, the invention is equally applicable to devices utilizing other means of dispensing medication such as programmable or nonprogrammable pumping or metering means as will be familiar to those of skill in the art. The manifold 13, the reservoir 14, the cover 16, and the flow regulator 30 may all be bonded or assembled to the bulkhead 15 in any suitable way, as will be described in more detail below. The cover 16, manifold 13 and bulkhead 15 together form an external housing of the medication delivery device.

The bulkhead 15 may have a hollow neck 17, a base 18, a number of through holes 19, a flow regulator mounting cavity 20; an outlet housing 21, an outlet conduit 22, and an outlet port 23. Although ten through holes 19 are illustrated in FIG. 1, there may be fewer, or more, through holes 19.

Although the bulkhead 15's neck 17, base 18 and outlet housing 21 are illustrated as being made as one integral component, they may be manufactured as separate components, and then bonded or assembled together in any suitable way. Similarly, although the outlet port 23 is illustrated as being made as a separate component, which is then bonded or assembled to the outlet housing 21, the outlet port 23 and the outlet housing 21 may be made as one integral component.

Although not illustrated, for clarity, the medication delivery device 10 may be equipped with any suitable means for preventing back flow of any fluid into the outlet port 23, such as a check valve. The means for preventing back flow of any fluid into the medication delivery device 10's outlet port 23 may be mounted in any suitable location, either internally or externally of the device 10, such as in its outlet conduit 22 or adjacent to its outlet port 23.

Although also not illustrated, for clarity, the medication delivery device 10 may be equipped with any suitable means for permitting or preventing flow of the medication 12 out of the outlet port 23, such as an on-off valve. The means for permitting or preventing flow of the medication 12 out of the outlet port 23 may be mounted in any suitable location, either internally or externally of the device 10, such as in its outlet conduit 22 or adjacent to its outlet port 23.

The bulkhead 15's hollow neck 17 may have an inlet 28. Housed within the neck 17 may be a septum 29, which may be held in place by any suitable means, such as by a threaded hollow plug 31 or by an interference (press) fit between the neck 17 and the plug 31, or by welding the neck 17 to the plug 31. The septum 29 may be made from any suitable resilient, self-sealing material which may be pierced by a needle, such as silicone rubber. Neck 17, inlet 28 and septum 29 together comprise a refill port which enables reservoir 14 to be filled and refilled with medication in a manner described more fully hereafter.

Also housed within the neck 17 may be any suitable filter 33, which may be bonded or assembled within the neck 17 in any suitable way. For example, as seen in FIG. 2, the filter 33 may be held within the neck 17 by being sandwiched between the neck 17's shoulder 63 and the manifold 13's ribs 27.

The filter 33 may be selected to filter particles from the medication 12 of a size which might clog, or otherwise harm, any of the device 10's components which are located downstream from the filter 33; or which might clog, or otherwise harm, whatever is receiving the medication 12 from the device 10. For example, if the device 10 is to be used for medical or veterinary purposes, the filter 33 may be selected to filter out particles as small as bacteria, or even as small as viruses, to help protect the patient or animal from the possibility of infection. By way of further example, if the filter 33 is located upstream from the fluid flow regulator 30, then the filter 33 may serve the dual functions of filtering out harmful bacterial or viruses from the medication 12, and of filtering out any particles from the medication 12 which might clog, or otherwise harm, the fluid flow regulator 30 and/or flow restrictor and keep it from operating properly.

Although the filter 33 is illustrated as being located within the bulkhead 15's neck 17, it could be placed in any other suitable location within the medication delivery device 10 which is upstream from where the outlet port 23 exits the device 10, such as in the reservoir 14, the through holes 19, the manifold 13's inlet recess 25, the manifold 13's outlet channels 26, the flow regulator mounting cavity 20, the outlet conduit 22, or the outlet port 23.

Alternatively, the filter 33 may be placed externally of the medication delivery device 10 in any suitable location, such as upstream from the neck 17's inlet port 28, or downstream from the device 10's outlet port 23. In such an event, the neck 17's shoulder 63 may be eliminated, since it would no longer be needed to hold the filter 33 in place within the neck 17.

The flow regulator 30 may be bonded or assembled to the bulkhead 15's regulator mounting cavity 20, over the outlet conduit 22, in any suitable way. Alternatively, the flow regulator 30 may be placed within the device 10 in any other suitable location which is downstream from the reservoir 14, the outlet conduit 22, or the outlet port 23.

Alternatively, the flow regulator 30 may be placed externally of the medication delivery device 10 in any suitable location, such as downstream of the outlet port 23. In such an event, the flow regulator mounting cavity 20 may be eliminated.

The flow regulator 30 may be any suitable fluid flow regulator which is selected to have the particular fluid flow characteristics which are desired for the particular intended use of the medication delivery device 10. For example, in order to help prevent an overdose of medication from being delivered to a patient by the device 10, the flow regulator 30 may be selected to provide a predetermined maximum flow rate of the medication 12, despite an overpressure of the medication 12 within the reservoir 14 which exceeds the normal operating parameters of the device 10. Such an overpressure might occur if, for example, the reservoir 14 was overfilled with the medication 12.

The manifold 13 may be bonded or assembled to the periphery of the bottom of the bulkhead 15's base 18 in any suitable way, and may form the bottom of the medication delivery device 10. The manifold 13 may have a cutout 24, an inlet recess 25, a number of outlet channels 26, and a number of ribs 27. The cutout 24 may be sized to accommodate the bulkhead 15's outlet housing 21. The ribs 27 may separate the outlet channels 26 from each other, and may help to hold the filter 33 within the bulkhead 15's neck 17. One end of each of the outlet channels 26 may be in fluid communication with the inlet recess 25, while the other end of each of the outlet channels 26 may be in fluid communication with a respective through hole 19 in the bulkhead 15.

Although ten outlet channels 26 and nine ribs 27 are illustrated, there may be fewer, or more, outlet channels 26 and ribs 27. Although the manifold 13's inlet recess 25 and outlet channels 26 are illustrated as being separate components, the outlet channels 26 may be eliminated and replaced by an enlarged inlet recess 25 which fluidly communicates with the bulkhead 15's through holes 19; and the inlet recess 25 may be eliminated and replaced by enlarged outlet channels 26 which are in fluid communication with the bulkhead 15's hollow neck 17.

The reservoir 14 may have a central aperture or hole 35, pleated inner and outer sides 37, 39, and an open bottom having inner and outer mounting flanges 41, 43. The reservoir 14 may be bonded or assembled to the bulkhead 15 in any suitable way; such as by bonding or assembling its inner mounting flange 41 to the outside of the base of the neck 17, and by bonding or assembling its outer mounting flange 43 to the inside of the bulkhead 15's peripheral lip 45. As a result, the bulkhead 15's base 18 forms the bottom of the reservoir 14, and the medication 12 may enter the reservoir 14 through the holes 19 in the base 18.

The use of a donut-shaped reservoir 14, with the bulkhead 15's neck 17 extending through the reservoir 14's central hole 35, may be preferred. This is because such a construction results in an unusually compact medication delivery device 10 while retaining sufficient medication storage capacity. This arrangement provides a compact radially adjacent or side-by-side positioning of the reservoir and the refill port which does not add to the thickness of the medical delivery device in the direction of the longitudinal axis of the housing. Such compactness may be particularly desirable for the device 10 in certain circumstances, such as if it is designed to be implanted within a patient's body. Although the reservoir 14 and its central hole 35 are illustrated as having circular shapes, they could have any other suitable rounded or angular shape, such as oval, square or rectangular. Additionally, instead of being positioned concentrically with the longitudinal axis of the housing at the center of reservoir 14 as illustrated, hole 35 could be offset to any desired nonconcentric location.

The reservoir 14's pleated inner and outer sides 37, 39 permit the volume of the reservoir 14 robe varied. For example, as seen in FIG. 2, when the reservoir 14 is full, then its pleated inner and outer sides 37, 39 unfold a maximum amount, thereby permitting the reservoir 14's top 61 to be located a maximum distance from the bulkhead 15's base 18, which forms the bottom of the reservoir 14.

Figure 4:
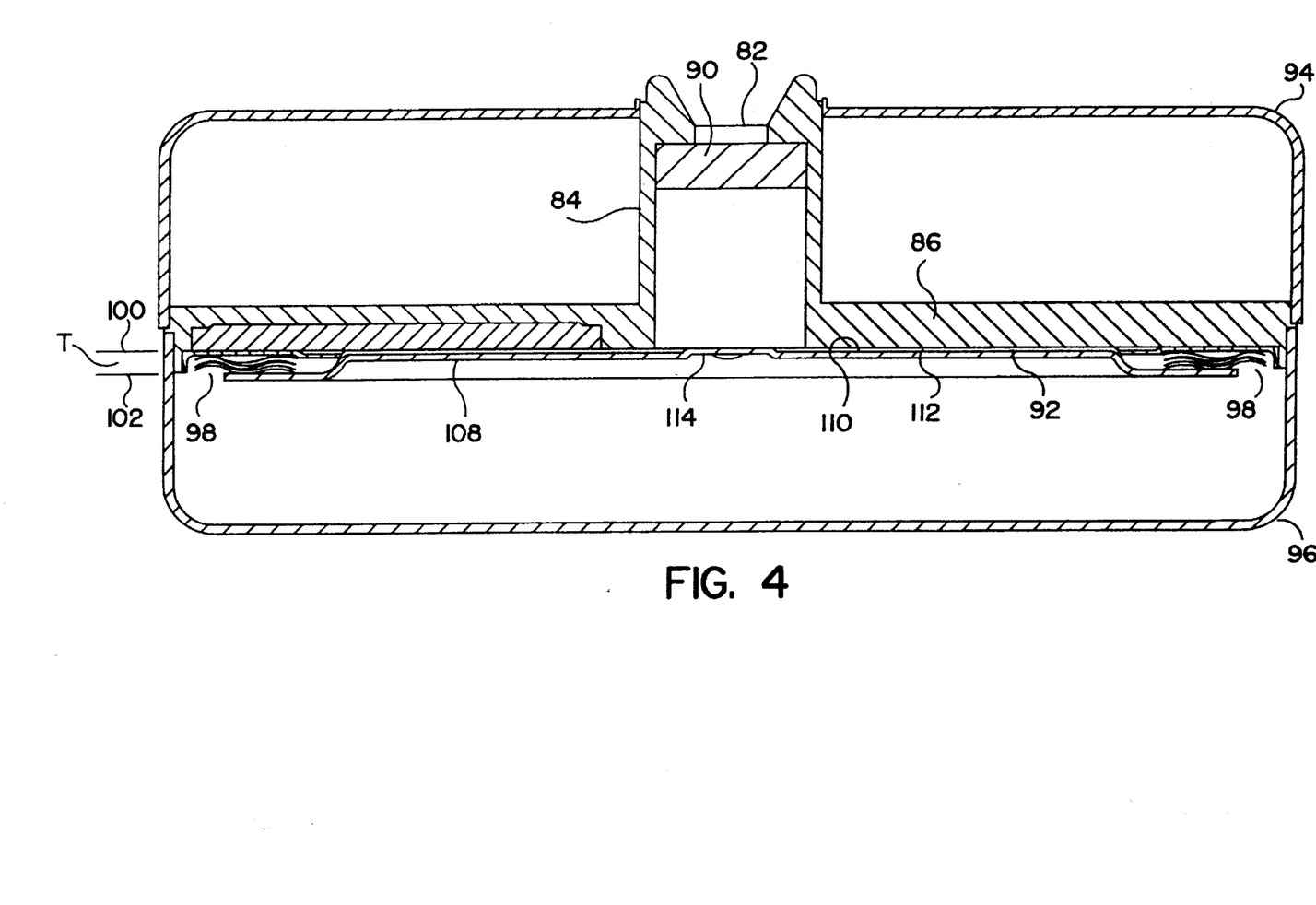
FIG. 4 is a cross-sectional view similar to that of FIG. 3 but incorporating the reservoir in terminal configuration of the present invention.
Figure 5:
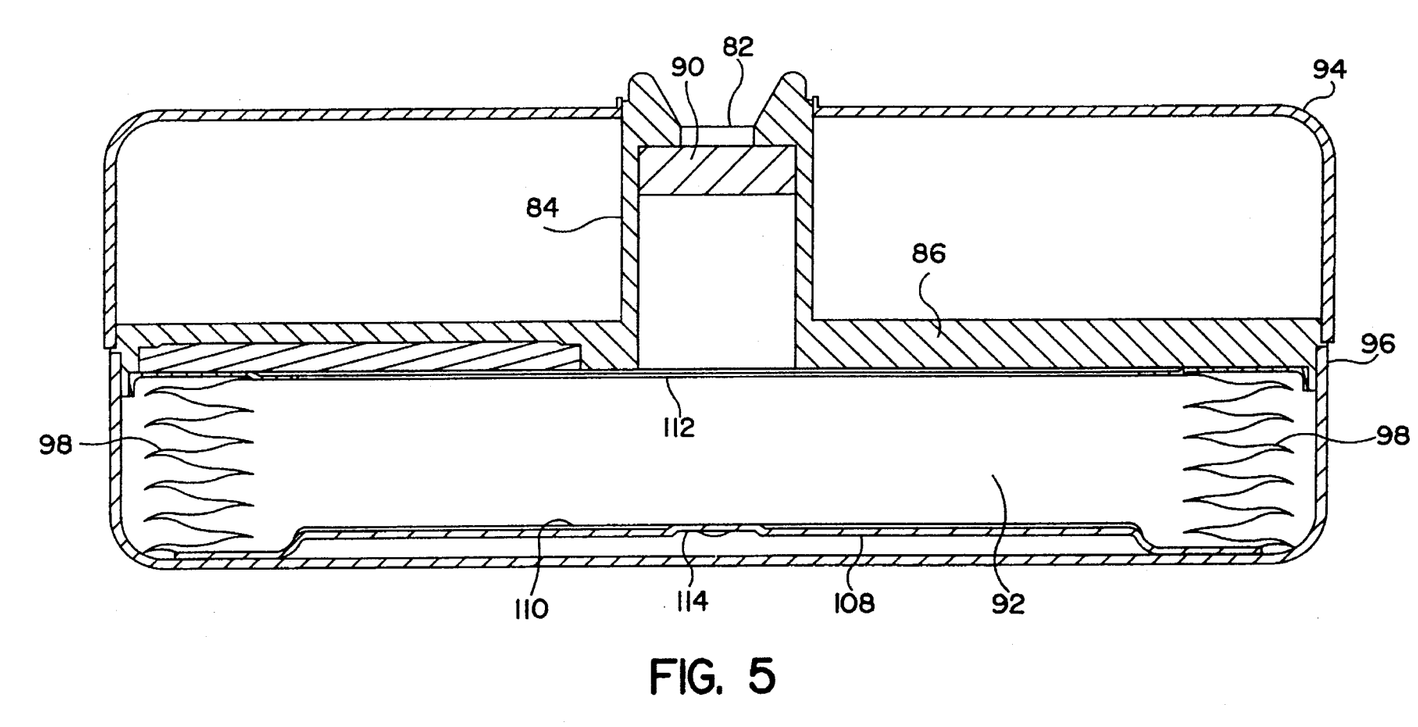
FIG. 5 is a cross-sectional view of the medication delivery device of FIG. 4 with the pleated reservoir in the full or expanded position.

As will be more fully described with respect to FIGS. 4 and 5 which show another embodiment of the invention, when the reservoir 14 is empty or evacuated, its pleated inner and outer sides 37, 39 fold up a maximum amount, thereby permitting the reservoir 14's end terminal consisting of top 61 and indented portion 72 to be located a minimum distance from the bulkhead 15's base 18. Base 18 may comprise a slightly raised boss as shown or may be flat. If base 18 is flat (as in the embodiment of FIGS. 4 and 5) indented portion 72 may be indented further towards bulkhead 15.

The cover 16 may have a central hole 47 for the bulkhead 15's neck 17; and inner and outer mounting flanges 49, 51. The cover 16 may be bonded or assembled to the bulkhead 15 in any suitable way, such as by bonding or assembling its inner mounting flange 49 to the outside of the top of the neck 17, and by bonding or assembling its outer mounting flange 51 to the outside of the bulkhead 15's peripheral lip 45.

A positive pressure may be imparted to the medication 12 within the reservoir 14 in any suitable way. For example, the space 53 between the reservoir 14 and the cover 16 may be pressurized in any suitable way, such as by locating in the space 53 a quantity of any suitable, volatile substance which has a relatively high vapor pressure at the intended operating temperature range of the medication delivery device 10. The suitable, volatile substance may, for example, be Freon 87, which has a gas liquid-gas vapor pressure of 3.9 PSIG at 37° C. or R-11 which has a vapor pressure of 8.4 PSIG at 37° C. Alternatively, the space 53 may be pressurized by filling it with a compressed gas.

Alternatively, a positive pressure may be imparted to the medication 12 within the reservoir 14 by making the reservoir 14 to be self-collapsing, such as by fabricating the reservoir 14 from an elastic material which is stretched when the reservoir 14 is filled with the medication 12.

Alternatively, a positive pressure may be imparted to the medication 12 within the reservoir 14 by using an external mechanical force to collapse the reservoir 14, such as by locating a spring between the reservoir 14's top 61 and the inside of the cover 16.

The medication delivery device 10 may be initially filled with the medication 12 in any suitable way, such as by first inserting a hollow needle 55 through the neck 17's septum 29, and into the space 57 which is located between the septum 29 and the filter 33. Any undesired perforation of the filter 33 by the needle 55 may be prevented in any suitable way, such as by providing a space 57 between the septum 29 and the filter 33. In addition, the needle 55 may be selected to be of the type which has a relatively blunt end, with an outlet hole 59 on its side. Further, although not illustrated for clarity, a perforated needle stop may be located in the neck 17 between the septum 29 and the filter 33. The size of the perforations in the needle stop may be selected to be small enough to prevent the passage of the needle 55 therethrough; but large enough to permit the free passage of the medication 12 therethrough.

A vacuum may then applied to the needle 55 until all of the air in the space 57, the filter 33, the inlet recess 25, the outlet channels 26, the through holes 19, the reservoir 14, the flow regulator 30, the outlet conduit 22, and the outlet port 23 has been evacuated. The check valve, which was mentioned above, may be used to prevent air from flowing into the medication delivery device 10 through its outlet port 23 during the evacuation process. The needle 55 may then be withdrawn, and the septum 29 will automatically reseal itself, thereby not admitting any air into the device 10.

A new needle 55, connected to a source of medication 12, may then be inserted through the septum 29 into the space 57. The source of the medication 12 for the needle 55 may be pressurized. The medication 12 will then be drawn into and/or forced into the medication delivery device 10 through the needle 55, and fill the space 57, the filter 33, the inlet recess 25, the outlet channels 27, the through holes 19, the reservoir 14, the flow regulator 30, the outlet conduit 22, and the outlet port 23. After the medication delivery device 10 has been filled with the desired amount of the medication 12, the on-off valve, which was mentioned above, may be used to prevent the medication 12 from leaking out of the outlet port 23. The needle 55 may then be withdrawn, and the septum 29 will automatically reseal itself, to prevent any medication 12 from leaking out of, and any air from leaking into, the space 57.

Once the desired amount of the medication 12 has been inserted into the medication delivery device 10, any suitable delivery means, such as a catheter, may then be attached in any suitable way to the medication delivery device 10's outlet port 23, for conveying the medication 12 from the outlet port 23 to the location where the medication 12 is to be delivered. The on-off valve, which was mentioned above, may be turned on long enough to permit the medication 12 to flow out of the outlet port 23 until any undesired air in the outlet port 23 and the delivery means has been purged; at which time the on-off valve may then be turned off.

The medication delivery device 10 may then be secured in any suitable way in its location of intended use, such as by inserting it within a patient's body. The free end of the delivery means, such as the free end of the catheter, may then be secured in any suitable way at the location where the medication 12 is to be delivered.

Once the device 10 and the free end of the delivery means have been secured in their desired location, the on-off valve may be turned on. That will permit the pressurized medication 12 in the reservoir 14 to flow out of the reservoir 14 and through the flow regulator 30, the outlet conduit 22, the outlet port 23, the delivery means. The rate of flow of the medication 12 from the reservoir 14 is governed by the flow regulator 30.

After a period of use, the reservoir 14 may be refilled with medication 12 in any suitable way, such as by the use of a needle 55 in a manner similar to that described above. Since the medication delivery device 10 maybe installed within a patient's or animal's body, the needle 55 may be used to fill the reservoir 14 without removing the device 10 from the patient or animal, by simply inserting the needle 55 into the septum 29, through the patient's or animal's skin.

In order to further reduce the weight and dead space of medication delivery device 10, there is incorporated a unique reservoir end terminal configuration. As discussed previously with reference to FIG. 2 the end terminal consists of top 61 of bellows reservoir 14 which has an indented surface portion 72 which extends inwardly towards manifold 13. When reservoir 14 is compressed an empty indented surface portion 72 insures that reservoir 14 more completely empties as will be explained in more detail with reference FIGS. 3–5 which illustrate the applicability of the invention to a conventional medication delivery device.

Figure 3:
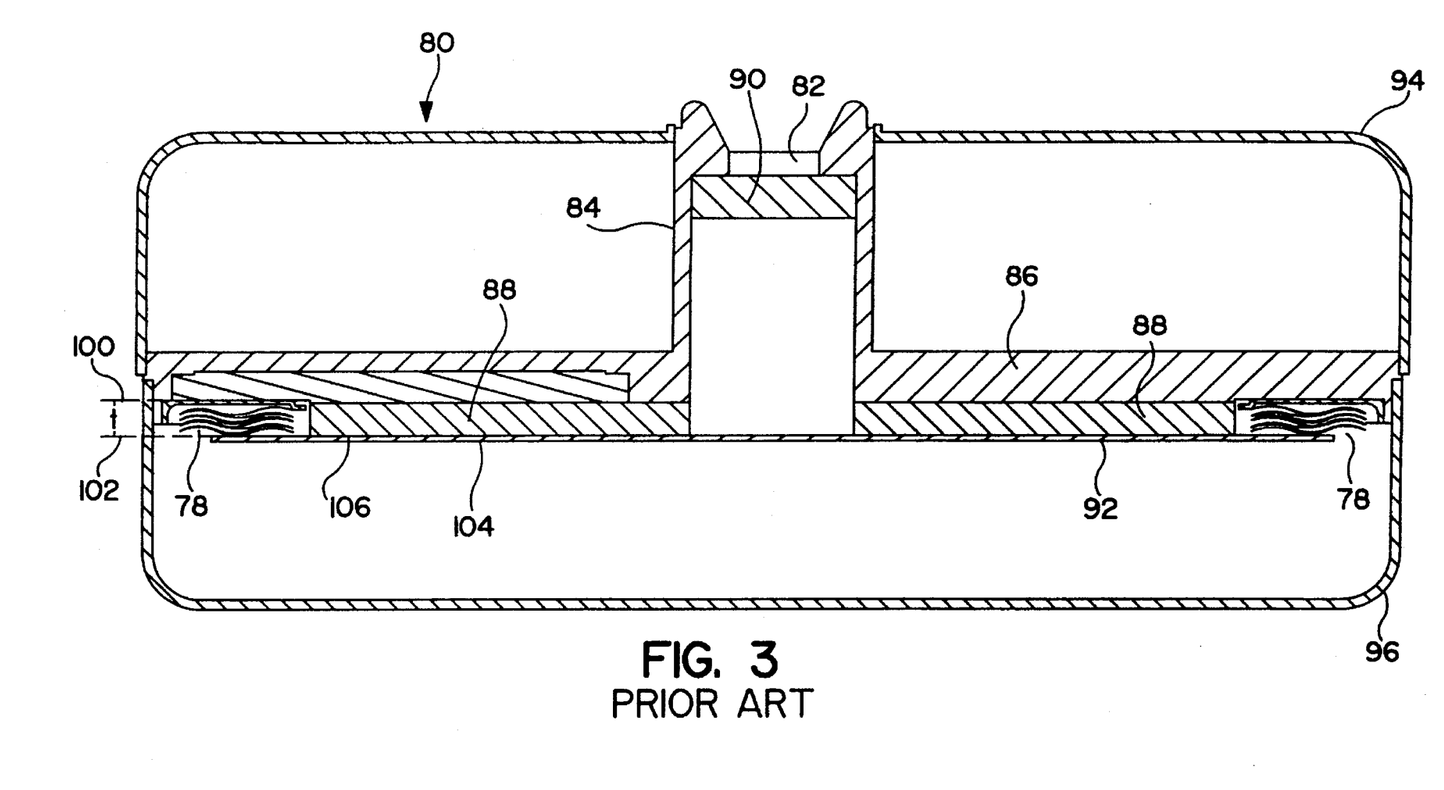
FIG. 3 is a cross-sectional view of a typical prior art medication delivery device having a pleated reservoir in the collapsed or empty position.

With reference to FIG. 3 there is shown a prior art medication delivery device 80. Device 80 includes an inlet 82 formed from a hollow neck portion 84 which may be an integral part of a bulkhead 86. Bulkhead 86 includes a raised portion or boss 88 which is usually an integral portion of bulkhead 86. A septum 90 is housed within neck portion 84. Device 80 includes a conventional bellows reservoir 92 (as opposed to the doughnut-shaped reservoir 14 of delivery device 10) which, in FIG. 3, is shown in the collapsed or empty position. A two piece cover or housing is comprised of an upper cover 94 and lower cover 96. For purposes of clarity, other components of device 80 are not illustrated since they are not necessary for an understanding of the present invention. Device 80 may be any conventional medication delivery device such as the Synchromed® Drug Pump manufactured by Medtronic, Inc., Minneapolis, Minn. The manner in which the medication is dispensed (i.e. flow regulation, flow restriction, pumping, metering) is not critical to the present invention.

With continued reference to FIG. 3 it can be seen that when reservoir is 92 fully collapsed, it's pleated edges 98 occupy a space t between lines 100 and 102 which are extended from the top and bottom of the pleats 98 when viewed in the orientation of FIG. 3. Thus, in order to more completely empty the reservoir when it is in its collapsed state, a boss 88 has been included as part of bulkhead 86. Boss 88 is configured to extended into reservoir 92 a distance approximately equal to distance T. It can be seen that when collapsed, the inner surface 104 of reservoir 92 contacts the bottom surface 106 of boss 82 thus, insuring that reservoir 92 is more nearly voided of medication when in the collapsed or empty position.

Although providing boss 88 on bulkhead 86 has solved the problem of being able to more nearly empty the pleated reservoir when in the collapsed position, it is a solution which has led to other problems. For example, boss 88 is usually formed as an integral part of bulkhead 86. Since bulkhead 86 is typically made of a metal such as titanium or Ti-6A1-4V a difficult machining step must be included in manufacturing the device in order to machine the bulkhead to its final configuration including boss 88. Additionally, boss 88 adds significant additional weight to the device. Since the medication delivery device is meant to be implanted in a patient, even a small increase in weight is undesirable. Conversely, even a small decrease in the weight of the device as shown in the embodiment of FIG. 2 is desirable.

Referring now to FIGS. 4 and 5, there is shown another embodiment of a medication delivery device which solves the above discussed problems of emptying a bellows reservoir without adding to the overall weight of the device. FIG. 4 is a cross-sectional view of a medication delivery device similar to that shown in FIG. 3 but incorporating the novel reservoir end terminal design of the present invention. FIG. 5 is a cross-sectional view of the device of FIG. 4 but with the bellows reservoir in its fully expanded position as it would be when full of medication. Like reference numerals are used in FIGS. 4 and 5 to identify like components. As best seen in FIG. 4, instead of including a boss on bulkhead 86, reservoir 92 is provided with an indented surface portion 108 which lies generally between pleats 98. Indented surface portion 108 extends into reservoir 92 in the direction of bulkhead 86 a distance which is approximately equal to distance T. Therefore, the upper surface 110 of raised surface portion 108 generally meets with the lower surface 112 of bulkhead 86 such that when reservoir 92 is in the collapsed/empty position nearly all of the fluid medication in the reservoir is evacuated. Optionally, indented surface portion 108 is provided with a ridge or dimple 114 to reduce the surface tension between surfaces 110 and 112. By indenting indented surface portion 108 by an amount approximately equal to T, the need of including a boss on the bulkhead is eliminated. Alternatively, the size of the boss on the bulkhead may be reduced as in the embodiment of FIG. 2. In either case, the weight of the device is decreased.

Within the scope of the present invention, the medication delivery device 10, as well as its various components, may have many alternative shapes, arrangements and variations. For example, instead of the device 10 having an overall circular or cylindrical shape, it could have any other suitable rounded or angular shape, such as oval, square or rectangular. In addition, instead of the device 10 having a concentric arrangement in which the bulkhead 15's neck 17 is located within the reservoir 14's hole 35, the reservoir 14 may not have a hole 35, and the neck 17 may be located along side of and substantially surrounded by the reservoir 14.

All of the medication delivery device 10's components may be made from, and bonded or assembled with, any suitable, durable, stable, corrosion-resistant substances which are compatible with the medication 12; which are compatible with the intended environment in which the device 10 is intended to be used; and which are compatible with the person, animal or thing with which the 10 is intended to be used.

The manifold 13; the cover 14; and the bulkhead 15's neck 17, base 18, outlet housing 21, outlet port 23 and plug 31 may be made from any suitable material which is also relatively rigid, such as plastic, ceramic, or metal. A suitable metal may be commercially pure titanium or Ti-6A1-4V.

The reservoir 14 may be made from any suitable material which is also relatively flexible (for proper operation of its pleated inner and outer sides 37, 39), such as plastic, or metal. A suitable metal may be commercially pure titanium or Ti-6A1-4V.

In addition, if the medication delivery device 10 is to be used in a medical or veterinary context, all of the device 10's components may be made from, and bonded or assembled with, substances which are compatible with at least one suitable sterilization process, such as heat sterilization (e.g., steam autoclaving), gas sterilization (e.g., ethylene oxide), liquid sterilization (e.g., hydrogen peroxide); or radiation sterilization (e.g., gamma radiation).

Any of the medication delivery device 10's components may be assembled together in any suitable leak-proof way, with or without gaskets, such as by using any suitable mechanical fastening means. For example, the plug 31 may be connected to the neck 17 with threads, in which case the septum 29 may act as a gasket for the plug 31. Further, the flow regulator 30 may be secured within the flow regulator mounting cavity 20 by the use of an O-ring gasket and any suitable mechanical clamping mechanism.

In addition, any of the medication delivery device 10's components may also be bonded together in any suitable leak-proof way, such as by using any suitable welding process, such as laser welding. For example, the outer edge of the manifold 13 may be welded to the bottom of the periphery of the bulkhead 15's base 18; the outlet port 23 may be welded to the bulkhead 15's outlet housing 21; the reservoir 14's inner and outer mounting flanges 41, 43 may be welded to the bulkhead 15's neck 17 and lip 45, respectively; and the cover 16's inner and outer mounting flanges 49, 51 may be welded to the bulkhead 15's neck 17 and lip 45, respectively.

Alternatively, any of the medication delivery device 10's components may also be bonded together in a leak-proof way, with or without gaskets, by using any suitable bonding materials, such as adhesives, glues and epoxies.

Alternatively, any of the medication delivery device 10's components may be bonded together in a leak-proof way with any suitable anodic bonding process. For example, the flow regulator 30 may be anodically bonded to the regulator mounting cavity 20 if the flow regulator 30's base 11 and the regulator mounting cavity 20's bottom 60 are made from, or have applied thereto in any suitable way, any suitable respective materials which may be anodically bonded together, such as silicon or titanium and 7740 Pyrex® glass made by the Corning Company of Corning, N.Y..

Alternatively, if the regulator's base 11 and the cavity's bottom 60 are not made from, or coated with, materials which may be anodically bonded directly together, then a layer of any suitable, compatible material which is anodically bondable with the regulator's base 11 and the cavity's bottom 60 may be inserted between the regulator's base 11 and the cavity's bottom 60 in any suitable way, before starting the anodic bonding process. For example, if both the regulator's base 11 and the cavity's bottom 60 were made from, or were coated with, 7740 Pyrex® glass (which will not anodically bond to itself), then the layer of suitable, compatible, anodic bonding material may be selected to be made from silicon.

It is understood that the foregoing forms of the present invention were described and/or illustrated strictly by way of non-limiting example.

In view of all of the disclosures herein, these and further modifications, adaptations and variations of the present invention will now be apparent to those skilled in the art to which it pertains, within the scope of the following claims.

I claim:

1. A medication delivery device comprising:

a housing, a reservoir within said housing, said reservoir having peripheral pleated side portions bounded by an end terminal and an opposing surface portion, said reservoir being movable from an expanded position to a compressed position, said end terminal having a surface portion which is indented in the direction of said opposing surface portion such that when said reservoir is in the compressed position there is substantially no separation between said indented surface portion and said opposing surface portion, said indented surface lying generally between said pleated side portions such that when said reservoir is in the compressed position nearly all of the fluid medication in the reservoir is evacuated by said indented surface, a reservoir refill port in fluid communication with said reservoir, an outlet port, means connected between said reservoir and said outlet port for dispensing medication from said reservoir through said outlet port.

2. The device of claim 1 wherein said dispensing means comprises a flow regulator.

3. The device of claim 1 wherein said reservoir includes an aperture within which said reservoir refill port is positioned.

4. The device of claim 1 wherein when said reservoir is in the compressed position said pleated side portion is collapsed such that the distance between said end terminal and said opposing surface is equal to a distance T, and wherein said indented surface portion is indented a distance approximately equal to distance T.

5. A medication delivery device comprising:

a housing, a bulkhead connected to said housing, said bulkhead including a base portion, a reservoir within said housing, said reservoir having a pleated side portion and an end terminal, said pleated side portion being connected to said base portion of said bulkhead such that said pleated side portion, said end terminal and said base portion together define an enclosed area, said reservoir being movable from an expanded position to a compressed position, said end terminal having a surface portion which is indented in the direction of said base portion such that when said reservoir is in the compressed position there is substantially no separation between said indented surface portion and said base portion, said indented surface lying generally between said pleated side portion such that when said reservoir is in the compressed position nearly all of the fluid medication in the reservoir is evacuated by said indented surface, a reservoir refill port in fluid communication with said reservoir, an outlet port, means connected between said reservoir and said outlet port for dispensing medication from said reservoir through said outlet port.

6. The device of claim 5 wherein said dispensing means comprises a flow regulator.

7. The device of claim 5 wherein said reservoir includes an aperture within which said refill port is positioned.

8. The device of claim 5 wherein when said reservoir is in the compressed position said pleated side portion is collapsed such that the distance between said end terminal and said base portion is equal to a distance T and wherein said indented surface portion is indented a distance approximately equal to distance T.

9. In a medication delivery device having a housing, a reservoir within said housing, said reservoir having peripheral pleated side portions bounded by an end terminal and an opposing surface portion, said reservoir being movable from an expanded position to a compressed position, said end terminal having a surface portion which is indented in the direction of said opposing surface portion such that when said reservoir is in the compressed position there is substantially no separation between said indented surface portion and said opposing surface portion, a reservoir refill port in fluid communication with said reservoir, an outlet port, and means connected between said reservoir and said outlet port for dispensing medication from said reservoir through said outlet port, the improvement comprising:

said indented surface lying generally between said pleated side portions such that when said reservoir is in the compressed position nearly all of the fluid medication in the reservoir is evacuated by said indented surface.

* * * * *

UNITED STATES PATENT AND TRADEMARK OFFICE
CERTIFICATE OF CORRECTION

PATENT NO. : 5,551,849
DATED : September 3, 1996
INVENTOR(S) : Christiansen, Chris It is certified that error appears in the above-indentified patent and that said Letters Patent is hereby corrected as shown below:

Col. 5, Line 8: "central aperture or hole" should be "central hole"

Col. 5, Line 39: "robe varied" should be "to be varied"

Col. 7, Line 23: "maybe" should be "may be"

Col 7, Line 60: "is 92 fully" should be "92 is fully"

Signed and Sealed this

Seventh Day of October, 1997

Attest:

BRUCE LEHMAN

Attesting Officer

Commissioner of Patents and Trademarks